United States Patent [19]

Uchigaki

[11] 4,304,119

[45] Dec. 8, 1981

[54] METHOD AND DEVICE FOR MEASURING THE FREEZING POINT LOWERING

[75] Inventor: Takatoshi Uchigaki, Kyoto, Japan

[73] Assignee: Kabushiki Kaisha Kyoto Daiichi Kagaku, Kyoto, Japan

[21] Appl. No.: 76,552

[22] Filed: Sep. 18, 1979

[30] Foreign Application Priority Data

Sep. 19, 1978 [JP] Japan ............................ 53-115494

[51] Int. Cl.$^3$ .......................................... G01N 25/06
[52] U.S. Cl. .................................................. 73/17 R
[58] Field of Search ............................... 73/17 R, 643

[56] References Cited

U.S. PATENT DOCUMENTS

| 3,173,289 | 3/1965 | Davis | 73/17 |
| 3,203,226 | 8/1965 | Fiske Jr. | 73/17 |
| 3,263,487 | 8/1966 | Fiske Jr. | 73/17 |
| 3,695,093 | 10/1972 | Hummel et al. | 73/17 |

OTHER PUBLICATIONS

Prager et al. "Freezing–Point Depression: New Method For Measuring Ultramicro Quantities of Fluids", in Science, 10/63, vol. 142, No. 3589, pp. 237–239.

Primary Examiner—Herbert Goldstein
Attorney, Agent, or Firm—Darby & Darby

[57] ABSTRACT

A method and device for measuring the osmotic pressure on the basis of an improved supercooling process, whereby and wherein cryohydrate nuclei are made to generate almost spontaneously in a part of a sample liquid by cooling the above part down further to a temperature (to an extra-supercooled state) lower than the temperature of a supercooled state, wherethrough the sample liquid as a whole is induced to freeze statically. Because of a non-necessity of using any stirring rod, it becomes possible to design a small-sized device, to reduce the sample liquid to be used to a possible infinitesimal, and further to perform the continuous measurement with the aid of the adoption of a flow cell.

14 Claims, 8 Drawing Figures

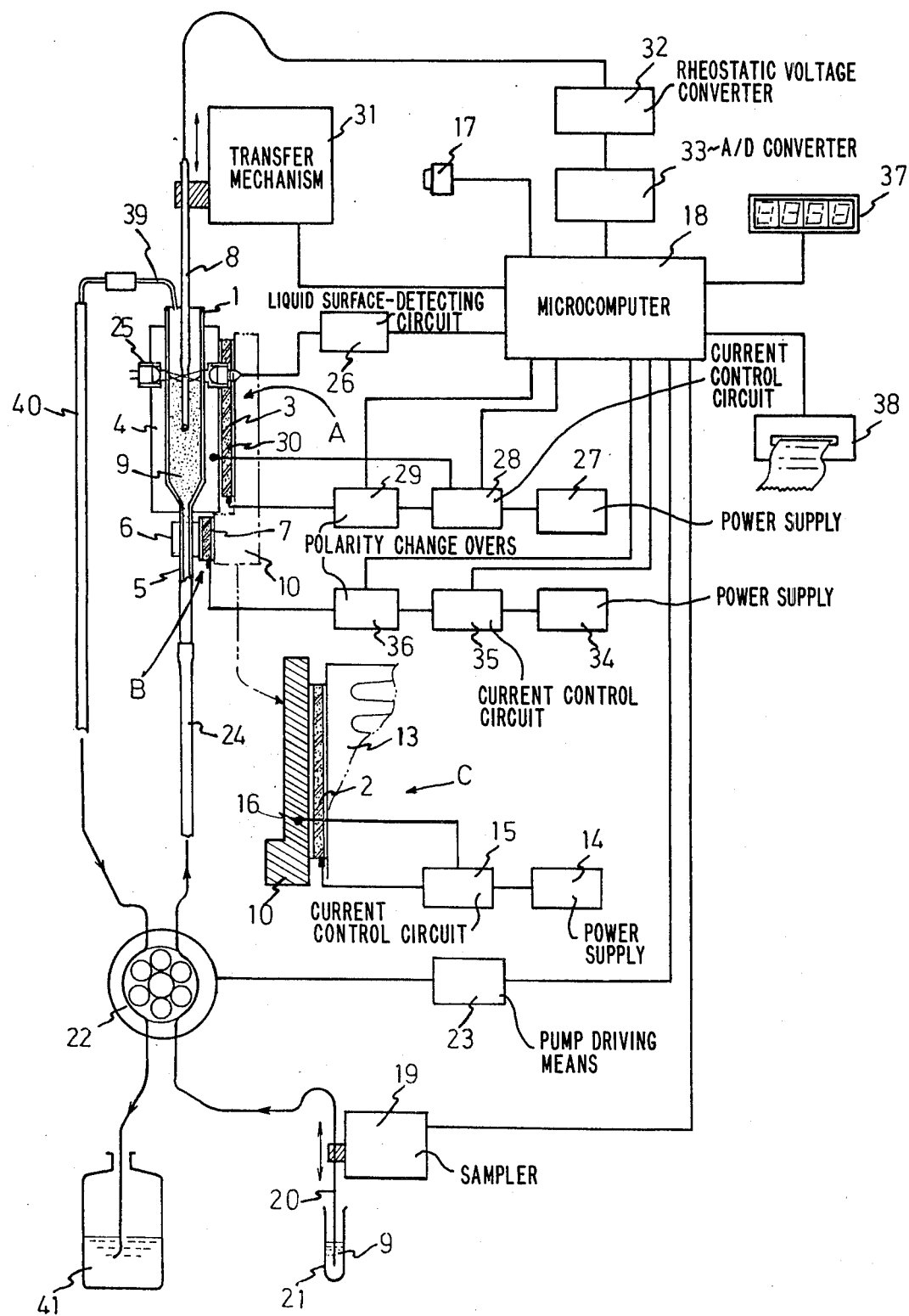

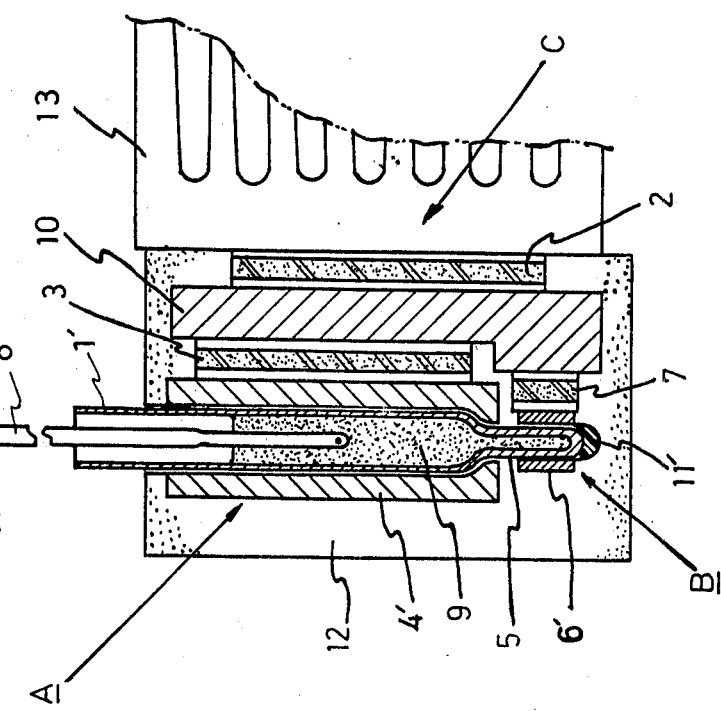
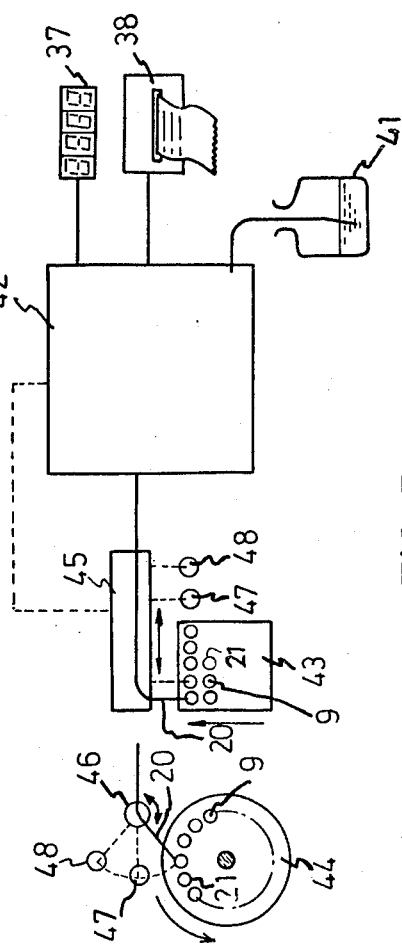
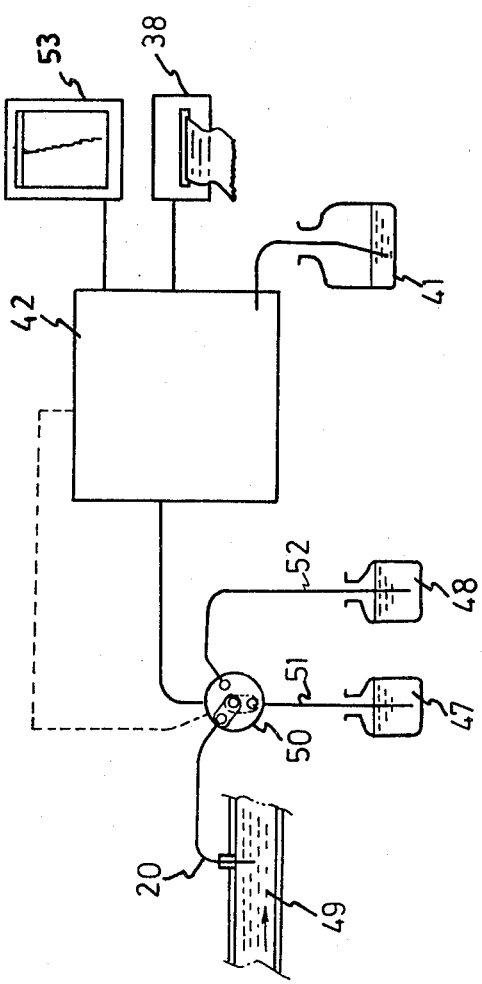

METHOD AND DEVICE FOR MEASURING THE FREEZING POINT LOWERING

BACKGROUND OF THE INVENTION

This invention relates to an improved method for measuring the freezing point lowering and also to a novel device being based on same, whereby and wherein a portion of a supercooled sample liquid is made to be changed further into a extra-supercooled state as a freezing stimulant to the whole supercooled sample liquid for the purpose of measuring the osmotic pressure of sample liquids, for example in particular, body fluids such as plasma, spinal fluid, tear and the like or dialyzed fluid as well as urine, which are the objects of clinical examination.

The living body is occupied by water up to about 60%. This water is present within the human body as plasma, cell fluid or the other body fluids in the state of dissolved substances of different species. Since the cell membrane of the living body is a semipermeable one, the osmotic pressure of the body fluids being dialyzed at the membrane has a great influence on the functions of the living body.

In consideration of such things, there have been recently brought to market one after another many kinds of devices for measuring the osmotic pressure of various body fluids or urine. The measurement of the osmotic pressure of plasma, urine, spinal fluid, etc. has come to be taken in daily examination, serving the purpose of diagnosing and controlling the patients who are suffering from dehydration, diabetes insipidus, hypochloremia, hyperchloremia, uremia, non-ketonic and high osmotic coma etc., etc. inclusive of the postoperative patients.

Seeking effective utilization, methods and devices for measuring the osmotic pressure should be able to operate on a dose of sample liquid being used for measuring the priceless spinal fluid which has been reduced or tear fluid to a possible infinitesimal. Such devices should also have the ability of quickly examining a great number of subject in a short time in an urgent need, and the possibility of the continuous measurement as of the dialyzed liquid which is inevitable at the time of the artificial dialysis.

However, the above-mentioned requirements are difficult to be fulfilled by any of a number of so-called devices for measuring the osmotic pressure now available on the market. Above all, it is impossible with them to perform the last referred-to continuous measurement. In addition, they contain further various points in question, as stated later. Under these circumstances, the appearance of a new type of method and device has been long eagerly waited for in this field.

The osmotic pressure in a solution is originally defined as the pressure produced by the diffusion of pure water into the solution which is partitioned by a semipermeable membrane. In the case of a dilute solution, like its other properties such as the freezing point lowering, the boiling point elevation, and the vapor pressure lowering, the osmotic pressure is directly proportional to the number of moles of the solute contained in the solution itself. Directly, it is measured with the use of the semipermeable membrane, but indirectly, it is determined by converting the values derived from any of the above-stated other three properties.

In the case of the body fluid, however, protein in it brings about heat coagulation if osmotic pressure is measured by the boiling point elevation process, otherwise it gives rise to a considerable error if osmotic pressure is measured by the vapor pressure lowering process, particularly when some volatile constituent such as alcohol is contained therein. Also it is impossible for the direct method to find out a suitable semipermeable membrane, as a result of which it takes a lot of time in measuring. Accordingly, the freezing point lowering method has come to be exclusively adopted.

What is called here as the freezing point lowering means a phenomenon where the freezing point of a solution becomes lower than that of a pure solvent in proportion to the mole concentration of a solute contained in the solution, as mentioned above, which is widely utilized for the molecular weight determination. It is the case with the osmotic pressure. It also is proportional to the number of molecules (atoms) contained in the solution, so that it becomes possible to find the osmotic pressure by measuring the degree of freezing point lowering, as shown in the following formula: (I)

$$\Delta Tf = \frac{R \cdot Tf}{1000 \cdot Io} \cdot C = Kf \cdot C \qquad (I)$$

whereat $\Delta Tf$ denotes the degree of freezing point lowering, R denotes the gas constant, Tf denotes the freezing point of the solvent (absolute temperature), Io denotes the melting latent heat per gram of the solvent, C denotes the molar number of the solute dissolved in 1 Kg of the solvent, and Kf denotes the depression of molar freezing point.

In the case where the solvent is water as the body fluid, the degree of freezing point lowering of the solution of the molar concentration 1 mol/Kg amounts to 1.858° C. (Kf=1.858° C.), and the freezing point is at −1.858° C. Contrary to this, when the freezing point of the solution reads −1.857° C., the molar concentration of it becomes 1 mol/Kg. Since the unit of osmotic pressure is the Osmol, the osmotic pressure of the solution of the molar concentration 1 mol/Kg can be expressed by 1 Osm/Kg. However, the osmotic pressure in the body fluid varies so very slightly that it is adequate to use the unit of 1:1000 of 1 Osm/Kg, that is, 1 m Osm.

Devices for measuring the osmotic pressure now in use all are composed of, for example, as disclosed in U.S. Pat. No. 3,203,226, a cooling tub to bring sample liquid into the supercooled state lower by several degrees than the freezing point, a head consisting of a bar thermistor for use in detecting the temperature of the freezing point and an electromagnetic vibratory stirring rod for the freezing, a measuring circuit, a controlling part, an indicating part, and others. In such a composition, the thermistor and the stirring rod are inserted into a test tube (discrete cell) containing the sample liquid. This test tube is dipped into the cooling tub to bring the sample liquid into a supercooled state. When the temperature of the sample liquid falls to −5°∼−6° C., the stirring rod is forced to hastily vibrate to generate cryohydrate nuclei therein, through which the sample liquid as a whole is caused to be frozen. At this time, the temperature of the sample liquid rises to the temperature of the freezing point through the evolution of the freezing latent heat, and is kept in the state of flatness for some time. After a while, it begins to fall gradually. The temperature at this flat part (plateau), that is, the temperature of the sample liquid which is in the state of coexistence of solid and liquid phases, is detected by means of the thermistor and displayed in the form of an osmotic pressure after being converted on the basis of the degree of freezing point lowering.

As stated above, existing apparatuses and methods of this kind can make the freezing point distinct by congealing the sample liquid after being supercooled while giving it a vibrative freezing stimulation, and they can measure the osmotic pressure with accuracy and in a relative short time with the use of a thermistor which is of a little heat capacity and able to detect exactly a slight difference in termperature. Inasmuch as a stirring rod is used for the freezing stimulation, however, they have still the following disadvantages:

(1) It is necessary to insert at the same time both the stirring rod and the thermistor for measuring the freezing point into the sample liquid, and consequently a relatively large-sized test tube must be used for it, as a result of which it is hard to reduce the sample tested to a microquantity. Even if the stirring rod and the thermistor both are tried to be miniaturized, a space of a certain extent is necessary all the same. Furthermore, there is a limit in such a miniaturization for the following reason:

In intensity of freezing vibration of the stirring rod is so considerably strong that the outside air is apt to be sucked into the sample liquid on occasion. Although the vibration time is as short as only about 1 second, the vibration in the progress of freezing exerts pressure on the thermistor amidst the state of coexistence of solid and liquid phases of the sample. As a result, restrictions are placed on the miniaturization of both the thermistor and the stirring rod from the viewpoint of the strength.

(2) The difficulty of miniaturizing the test tube and of reducing the sample tested to a microquantity is inevitably followed by having to make the compression refrigerating machine, Patier element, and others large-sized in order to enhance the cooling power, in company with which a large-sized means for air-cooling or water-cooling is also needed in order to exhaust efficiently the heat generated within the cooling means, therefore the prior apparatus as a whole is compelled to be made large-sized.

(3) In conventional apparatuses being equipped with a cooling tub using liquid refrigerant, the process and structure are apt to become complicated because there is a necessity now of gently stirring the sample liquid while cooling it with a view to making the measurement of the freeezing point easy by bringing the sample into a supercooled state as fast as possible. On the other hand it is desirable to elongate the plateau after freezing while keeping the temperature of the sample liquid constant. The sample is cooled uniformly by hastily cooling the cell-body until it reaches a suitable temperature while dipping it in liquid refrigerant and then slowly cooling the cell body while keeping it in cold air after pulling it up out of the liquid refrigerant.

(4) In these apparatuses, the stirring rod is exclusively employed as a freezing means, wherefore it is difficult for them to use a flow cell, and consequently to perform the continuous measurement or to measure a number of subjects in a short time. Existing apparatus all are in need of the respective tubes for each sample. In case of having constructed a kind of apparatus for the continuous measurement of one and the same sample, it is necessary for it to quantitatively pipet the sample liquid into the test tube each occasion, in consequence of which some specially-made pipetting means and transfer mechanism of test tubes come to be required, thereby entailing a flaw that the apparatus as a whole becomes structurally complicated and large-sized.

SUMMARY OF THE INVENTION

The present invention is to provide a method and device having very excellent properties whereby the defects of conventional apparatuses such as mentioned above can be eliminated once and for all, and which will fulfill all matters demanded of the before-stated method and device for measuring the osmotic pressure, thus making automatic control and digital representation possible.

That is, the method according to the present invention aims principally at being a system in which cryohydrate nuclei turn out almost spontaneously in a portion of sample liquid by cooling this portion lower (to the extra-supercooled state) than the supercooled temperature, thereby enabling it to induce the freezing of the whole sample liquid statically, instead of conventional freezing systems utilizing the mechanical vibration of the stirring rod.

In doing so, the measurement can be made by inserting merely a detecting instrument of temperature (thermometer) for measuring the equilibrium temperature as an essential object at the time of freezing into the sample liquid without the interposition of a mechanically vibrating member such as the stirring rod therein, thereby being able to reduce the sample liquid tested to a possible infinitesimal. The method according to the present invention is characterized further in that the particles once used in the sample liquid also are not so much destroyed because strong vibration is not given to the sample liquid itself, and consequently the sample can be utilized again as they are for measurement of the other item.

Being based on the freezing method which constitutes a characteristic feature of this invention, it is possible to miniaturize the measuring vessel (cell body), so that the application of this invention to conventional discrete types is proven to be effective (FIG. 6). Further, the invention of this application has succeeded in the structural simplification of the apparatus to a remarkable extent on the basis that the flow cell was adopted in the measurement system wherein the sample liquid was pipetted intermittently to be measured, so that there was no necessity of incorporating thereinto so many movable parts (FIGS. 1 and 2).

In conventional systems wherein liquid refrigerant was used as a cooling means, the refrigerant had to be replenished or exchanged at regular intervals, and also it took much time for taking out the refrigerant in case of transferring the apparatus. These disadvantages have been overcome by the invention of this application by directly cooling the cell body with the use of thermomodules and the like, instead of using liquid refrigerant in the capacity of a cooling means. Nevertheless, it is the matter of course that our invention which is distinct in the freezing means can be also applied to apparatuses of such a type that are using liquid refrigerant as a cooling means (FIG. 7).

BREIF DESCRIPTION OF THE DRAWINGS

The invention will now be described more particularly with reference to examples shown in the accompanying drawings, wherein:

FIG. 2 is a block diagram of another embodiment of the invention;

FIG. 4a shows an embodiment of the invention which can take measurements from a plurality of samples;

FIG. 4b shows a sample-transfer means which rotates a plurality of sample containers to permit measurements to be taken from each one;

FIG. 5 is a block diagram of another embodiment of the invention which takes and measures samples from a stream of sample liquid; and FIGS. 6 and 7 are vertical sectional views of two freezing point measuring parts which can be used in the invention.

DETAILED DESCRIPTION OF PREFERRED EMBODIMENTS

Figure 1:
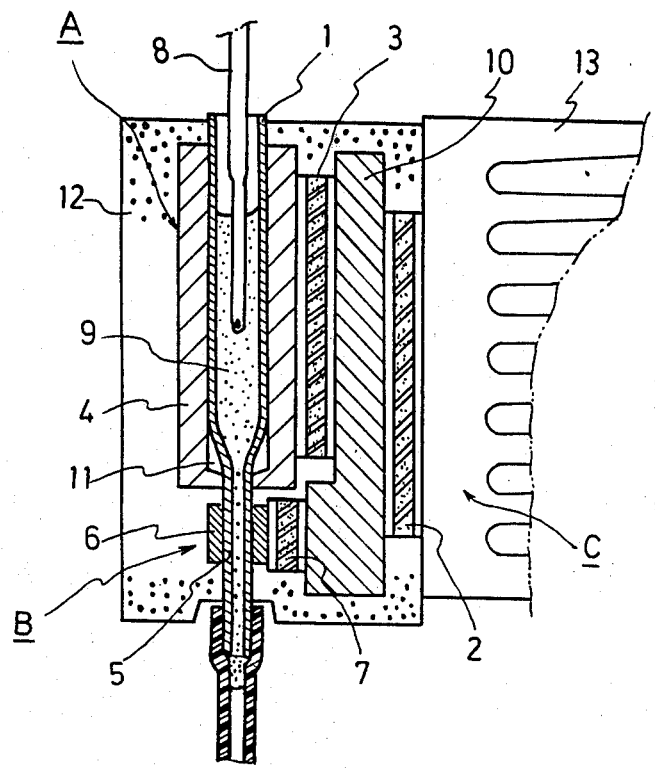
FIG. 1 is a vertical sectional view of that part of the present invention which measures the freezing point using a flow cell.

FIG. 1 is a vertical sectional view of a freezing point measuring part of a device according to the present invention, wherein a flow cell (1) preferably made of glass tube and the like is so constructed as to be cooled as far as the supercooled temperature through the interposition of a metallic flow cell block (4) by the cascade connection of thermomodule (2), (3) being based on the well-known principle of Pertier effect. A series of these cooling means forms a main cooling device (A). The lower part of the flow cell (1) is formed into a small tube part (5), which is cooled down to a lower temperature, that is, to an extra-supercooled state, through a metallic small tube block (6) by a thermomodule (7). The just now described cooling means is called a local cooling device (B). Cryohydrate nuclei are formed witin the small tube part (5). However, the structure of the extra-supercooling part of the cell body (1) is not always limited to such a small tube system. It does not matter if only it is so constructed that the temperature of the extra-supercooled part does not affect the measuring part, so that the measurement accuracy can be heightened. The flow cell block (4) and the small tube block (6) are made of metal having good thermal conductivity. In order to further the cooling process effectively, the thermomodules (3), (7) may be formed what with a cylindrical shape and what by arranging a plurality of them circlewise, respectively.

The flow cell (1) is constructed in such a manner that a thermistor (8) for detecting the temperature of the sample liquid can be inserted therein so as to be able to detect the temperature change of the sample liquid.

The measurement working of the apparatus of an example according to the present invention will now be described in detail with reference to FIGS. 1 to 3.

After putting on the power source, a cooling plate (10) is controlled to a low temperature by the outside cooling device (C) which is composed of the thermomodule (2), a power supplying means (14), a current control circuit (15), and a thermistor (16), and it is provided for effectively cooling the thermomodule (3) and the thermomodule (7). Incidentally, the reference numeral (11) in the figure indicates heat-conductive grease being interposed between the flow cell (1) and the flow cell block (4), the numeral (12) indicates insulating material which is enveloping the freezing point measuring part, and the numeral (13) indicates a radiator which is arranged close to the radiating side of the thermomodule (2).

Figure 3:
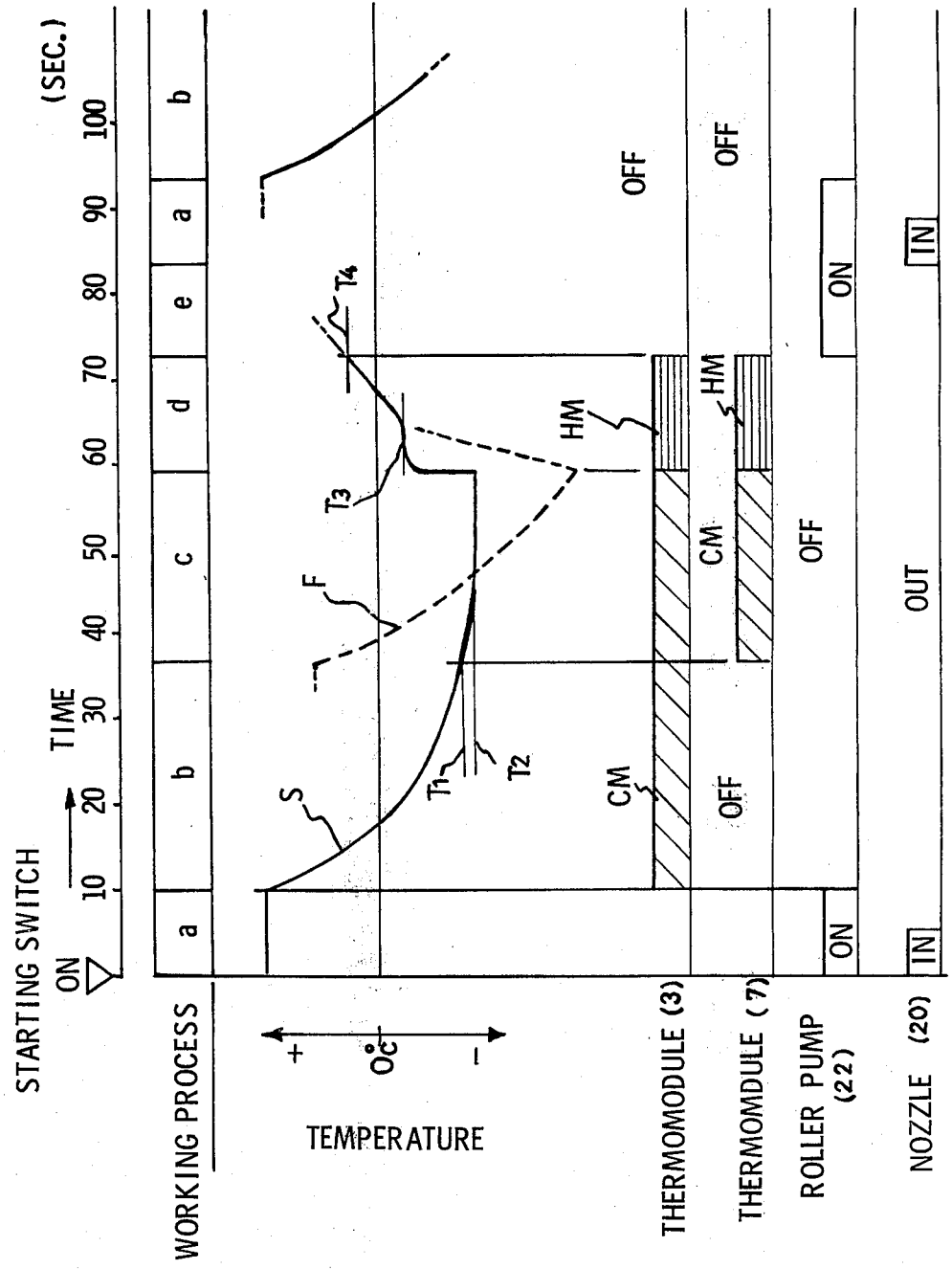
FIG. 3 is a chart showing the operation of the embodiment of FIG. 2 as a function of time.

Next, when a starting switch (17) is turned "ON", a sampler (19) begins to work by the indication of a microcomputer (18) as an arithmetic processing unit, a nozzle (20) is inserted into a sample container (21) [FIG. 3: nozzle "IN"], and at the same time when a roller pump (22) is rotated [FIG. 3: roller pump "ON"], the sample liquid (9) is introduced through a liquid-conveying duct (24) into a flow cell (1).

When the surface of the sample liquid (9) is detected by a photocoupler (25) and a liquid surface-detecting circuit (26), then the roller pump (22) comes to a stop by the indication of the microcomputer (18), and the introduction of the sample liquid is completed [FIG. 3, working process, a: "state of introduction of sample liquid"].

On the other hand, after the sample liquid is sucked up to the quantity necessary to fill up the cell body (1), the nozzle (20) is lifted, when an air layer in its turn is sent into the liquid-conveying duct (24) [FIG. 3: nozzle "OUT"]. Incidentally the reference numeral (23) in FIG. 2 indicates a pump-driving means.

When the introduction of the sample liquid is finished, a transfer mechanism (31) starts to work by the indication of the microcomputor 18, whereby the thermistor (8) is inserted into the sample liquid (9). Simultaneously with it, the main cooling device (A), which is composed of the thermomodule (3), a power supplying means (27), a current control circuit (28), a polarity change-over mechanism (29), and a thermistor (30), works to cool the flow cell body (1), and the temperature of the sample liquid begins thereby to fall [FIG. 3, working process b: "supercooled state"].

In this occasion, by adequately controlling the current flowing through the thermomodule (3) in accordance with the proportional control system, there can be attained the uniformly cooling effect similarly to the hastily or slowly conducted coolings in the case where conventional liquid refrigerants are used.

If the flow of the sample liquid is stable in the state where the thermistor (8) is being inserted therein, it is possible to incorporate the thermistor (8) into the flow cell (1), so that the above-mentioned transfer mechanism can be omitted. The temperature of the sample liquid is monitored by a rheostatic voltage converter circuit (32), an A/D converter (33), and the microcomputor (18), and when it reaches the working temperature T of the thermomodule (7) [FIG. 3: curve S] which has been stored beforehand in the microcomputer (18), the local cooling device (B) composed of a power supplying means (34), a current control circuit (35), a polarity change-over mechanism (36), and the thermomodule begins to work, commencing to cool the small tube part (5) of the flow cell [FIG. 3: curve F]. On the other hand, the temperature of the sample liquid gradually gets to the supercooled temperature T2 established in advance by the thermistor (30) and the current control circuit (28).

When the temperature of the small tube part (5) falls [FIG. 3: curve F] to about $-15° \sim -25°$ C., the freezing takes place almost spontaneously in this part to generate cryohydrate nuclei. With these as a start, the whole sample liquid comes rapidly to freeze [FIG. 3, working process, C: "state of generation of cryohydrate nuclei"]. The temperature at which this natural freezing takes place varies dependently upon the concentration of the sample liquid and others. But as the sample liquid here is cooled only locally, the influence of it upon the measured value can be ignored.

Concurrently with the freezing, the thermomodule (7) and the thermomodule (3) both are changed from the cooling mode (CM) to the heating mode (HM) by the polarity change-over mechanism (36) and the polarity change-over mechanism (29), respectively. The quantity of heat of each of the thermomodules (3), (7) is controlled with the current most favorable for the measurement beforehand programmed in the microcomputer (18).

The temperature of the sample liquid rises owing to the evolution of the latent heat consequent upon the freezing and reaches the plateau, but then it rises again gradually up to the reverse S-shaped change of temperature [FIG. 3, working process, d: "freezing, measurement, thawing"]. The freezing point temperature is measured by treating the minimum point T3 of the coefficient of variation being found through the differentiation of the reverse S-shaped curve with the use of the microcomputer as the equilibrium temperature in the state of coexistence of solid and liquid phases, and it is put out at an indicator (37) or a printer (38).

When the sample liquid begins to gradually thaw and the temperature of it reaches T4, it is judged that the sample liquid has been thawed as a whole. Then the roller pump (22) rotates [FIG. 3: roller pump "ON"], and the sample liquid is discharged [FIG. 3, working process, e: "discharge"]. The sample sucking-out mechanism consisting of a discharge nozzle (39), a discharge tube (40) and the roller pump (22) is provided only for helping the discharge, and the provision of it is not always required. Accordingly, it does not matter whether it is replaced by a system of making the sample liquid overflow direct from the flow cell or the liquid-introducing duct (24) is made to serve as a substitute for the discharge tube (40). The reference numeral (41) in the figure indicates a foul liquor vessel.

The reason why each of blocks (4), (6) is heated after the freezing in this example is that there is a necessity of bringing the frozen sample liquid again into the state of liquidness at the time of discharging it as a sequel to the employment of a flow cell in the capacity of the cell body. Therefore, as a heat source is being used the thermomodules are able to easily make the cooling and heating by changing-over the current. The controlling of the current of the thermomodules enables regulation of the cooling velocity with relative ease, and to cool the sample liquid (9) uniformly in accordance with the programming of the microcomputer (18), as described before.

FIG. 4(a) shows an example in which a measuring device for many subjects is incorporated. This device is constructed by connecting a well-known sample transfer means (43) able to translate in parallel a plurality of sample containers (21) . . . to the main body of a measuring section (42). In the figure, the reference numeral (45) indicates a sampler, and the numeral (47) indicates a detergent liquid. A suction nozzle (20) of the sampler (45) sucks up alternately the sample liquid (9) and the detergent liquid (47). The reference numeral (48) indicates a reference liquid. FIG. 4(b) shows another sample-transfer means (44) rotating and supplying the sample containers (21) . . . , and the numeral (46) indicates the sampler.

FIG. 5 shows another example designed as a continuous measurement device, wherein the nozzle (20) is inserted into a sample liquid flow (49) and sucks the sample liquid intermittently by a fixed quantity to measure the osmotic pressure in likewise as the above-mentioned. When the measurement is finished, the sample liquid is discharged from the flow cell (1), which is then washed with the detergent (47) sucked up through a nozzle (51) by a change-over valve (50), providing for the next measurement. The reference numeral (52) indicates a nozzle for the reference liquid. It is also good if a shift is taken so as to be able to do the continuous recording by means of a chart recorder (53) instead of a digital display device (37).

In these examples mentioned above, the flow cell is employed in the capacity of a cell body (measuring vessel). However, the freezing means according to the present invention can be applied, needless to say, to the case of the discrete cell of a conventional type. In such a case, as in the flow cell, it is possible to miniaturize the size of the apparatus and to reduce the quantity of the sample liquid to be used to a possible infinitesimal on the basis of the non-necessity of using the stirring rod.

The one shown in FIG. 6 is designed in such a manner that, just like the above-mentioned case, the discrete cell (1') is surrounded by a discrete cell block (4') of the main cooling device (A) and a small tube block (6') of the local cooling device (B) to be cooled by the thermomodules (2), (3), and (7), in connection with which the front end part (5') of the cell (1') is formed smaller so as to be easily frozen. However, unlike the case of the flow cell, it is not always required to be thawed after the freezing, so that it will do if each of the thermomodules (3), (7) is not changed over to the heating mode. Further, since the controlling of the cooling temperature can be made easily by each of the blocks (4'), (6') and of the thermomodules (3), (7), it is not necessary to move up and down the cell body each time of the hastily and slowly conducted coolings as in the case of using conventional liquid refrigerants, and in comparison the present device and process becomes quite simple.

Figure 7:
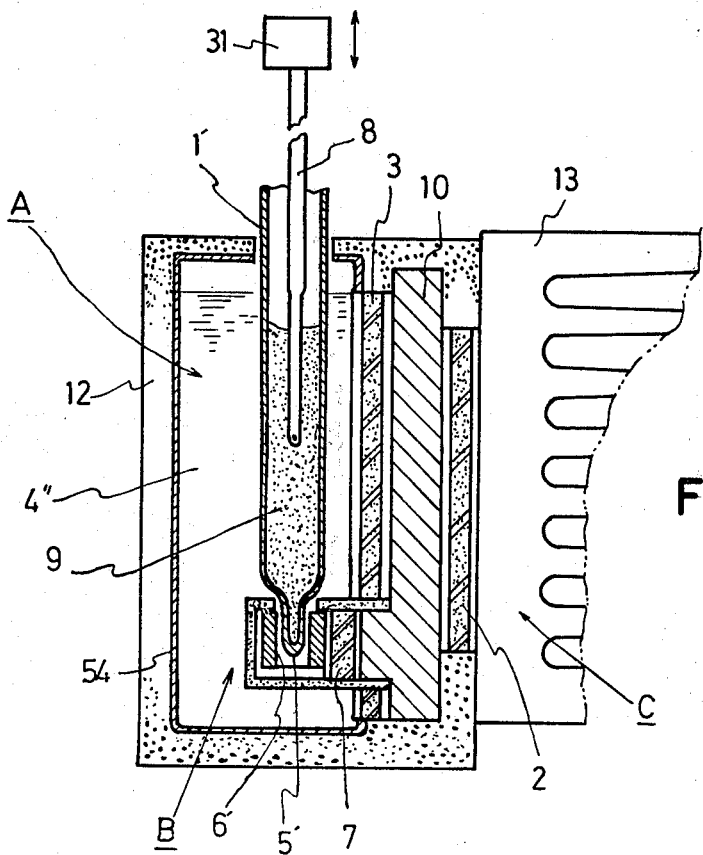

For all that, it is not that the employment of conventional liquid refrigerants is forbidden in the present invention. It does not matter whether they are used as a heat medium in a small quantity between the discrete cell (1') and the blocks (4'), (6'), or otherwise between the blocks and the thermomodules, as shown in FIG. 6, or whether they are used in the form of a liquid refrigerant (4") sealed in a refrigerant receptacle (54) as a substitute for the cell block (4') of FIG. 6, as shown in FIG. 7. However, in the latter case (FIG. 7), the simplification of the device and process is not as good as expected.

The method and device according to the present invention can be applied not only to the measurement of the osmotic pressure but also to the determination of the physical properties, such as, for example, molecular weight, obtained by finding the depression of freezing point. In this case, of course, the microcomputer must be programmed so as to be able to calculate the molecular weight from the degree of freezing point lowering in the room of the value of osmotic pressure.

The method of this invention is a method of measuring freezing point lowering through the utilization of supercooling, as mentioned above, wherein cryohydrate nuclei are caused to be generated almost spontaneously in a part of the sample liquid by cooling that part down to a temperature lower than the supercooled temperature. The whole liquid is thereby made to statically freeze with the thus-generated cryohydrate nuclei as a freezing means, so that there is no necessity of using a stirring rod in this method, in consequence of which it becomes possible to miniaturize the size of the cell and further to reduce the quantity of sample to be used to a possible infinitesimal. When by this method, the sample liquid is not at all spoiled and can be utilized again as it is, and the cooling devices are made compact in structure, the process of the measurement becomes simple.

In addition, the method according to the present invention has a further big advantage with respect to the use of a flow cell, whereby it becomes possible to continuously measure the osmotic pressure of the body fluids such as plasma, dialyzed fluid, urine, and the like, on one hand, and on the other, a number of different subjects in a short time, thus exhibiting significant utility in the field of clinical analysis.

The device and method according to the present invention has the excellent features and advantages of: measuring accurately a very small quantity of sample liquid irrespective of the individual differences by the adoption of a microcomputor; cooling a sample liquid uniformly without using any complicated device and process by employing thermomodules and metallic blocks as cooling means; continuously measuring many different samples and subjects many quickly through the use of a flow cell system; and simplifying each part of the cooling and measuring devices because of the smaller quantity of sample liquid to be used and the absence of any stirring means, in consequence of which the whole device can be miniaturized without difficulty.

What we claim is:

1. A method for measuring a freezing point, comprising the steps of:
    reducing the temperature of a sample liquid to a temperature representing a supercooled state;
    generating cryohydrate nuclei in a portion of said sample liquid by cooling said portion to a temperature lower than the temperature of said supercooled state, thereby to freeze said sample liquid using the cryohydrate nuclei as a freezing stimulant; and
    measuring the subsequent thermal arrest point of said sample.

2. A method for measuring a freezing point as set forth in claim 1, wherein the temperature of the frozen sample liquid, in a state of coexistence of solid and liquid phases, is measured continuously, the temperature at a minimum point of the coefficient of variation being calculated by an arithmetic processing unit and treated thereby as the sample freezing point temperature.

3. A method for measuring a freezing point as set forth in claim 1 or 2, wherein, on freezing, said sample liquid is permitted to warm toward a point of thawing.

4. The method of claim 1 comprising the steps of comparing the thermal arrest point of said sample with the freezing point of a standard liquid; and calculating the difference between the freezing point of said standard liquid and that of said sample.

5. An apparatus for measuring a freezing point comprising
    a container for holding a sample liquid;
    means for cooling all of the liquid of the sample to a temperature representing a supercooled state;
    means for cooling a portion of the sample to a temperature lower than the temperature of said supercooled state thereby to generate cryohydrate nuclei in said portion as a freezing stimulant to freeze the sample; and
    means for measuring the subsequent thermal arrest point of the sample.

6. The device of claim 5 wherein said means for measuring the freezing point of the sample comprises a thermistor exposed to said sample liquid, the signals from the thermistor being received and processed by an arithmetic processing unit thereby to control the supercooling means and said means for lowering the temperature of the sample below the supercooled temperature; said device including means for displaying the result operated and processed by said arithmetic processing unit.

7. The device as set forth in claim 6, wherein said container is a flow cell, and the device includes a sampler and a roller pump actuated by instructions from said arithmetic processing unit thereby to introduce a predetermined quantity of sample liquid into said flow cell.

8. The device as set forth in claim 7, wherein said sampler has a movable nozzle, which, after having withdrawn a predetermined quantity of said sample liquid in a first position, moves to imbibe air from a second position.

9. The device as set forth in claim 8, wherein said sample liquid container is mounted on a sample-transferring mechanism which rotates synchronously therewith whereby said nozzle withdraws sample liquid and a wash liquid alternately.

10. The device as set forth in claim 8, wherein said sampler comprises additional nozzles inserted into a wash liquid and a reference liquid, respectively, and a change-over valve for each of said additional nozzles.

11. Device as set forth in claim 6, wherein said container is a discrete cell; and wherein said cooling means for said sample and said cooling means for said sample portion are both constructed as capable of being cooled and heated, and include a transferring mechanism which moves said thermistor up and down.

12. The apparatus of claim 6 in which said processing unit actuates the cooling means for said portion of the sample upon the temperature of said sample reaching a predetermined supercooled state.

13. The apparatus of claim 5 comprising means for comparing the thermal arrest point of said sample with the freezing point of a standard liquid; and means for calculating the difference between the freezing point of said standard liquid and that of said sample.

14. The apparatus of claim 5 in which said container comprises a major section surrounded by the cooling means for said sample, and a minor section surrounded by the cooling means for said portion of the sample.

* * * * *